(12) United States Patent
Ito et al.

(10) Patent No.: US 6,856,917 B2
(45) Date of Patent: *Feb. 15, 2005

(54) DATA PROCESSING APPARATUS FOR CHROMATOGRAPH

(75) Inventors: Masahito Ito, Hitachinaka (JP); Kisaburo Deguchi, Hitachinaka (JP); Yoshiaki Seki, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/693,892

(22) Filed: Oct. 28, 2003

(65) Prior Publication Data

US 2004/0230381 A1 Nov. 18, 2004

Related U.S. Application Data

(63) Continuation of application No. 10/319,692, filed on Dec. 16, 2002, now Pat. No. 6,675,107, which is a continuation of application No. 09/940,636, filed on Aug. 29, 2001, now Pat. No. 6,529,836, which is a continuation of application No. 09/562,026, filed on May 1, 2000, now Pat. No. 6,314,374, which is a continuation of application No. 08/605,416, filed on Feb. 22, 1996, now Pat. No. 6,148,266.

(30) Foreign Application Priority Data

Feb. 27, 1995  (JP) ............................................... 7-37937

(51) Int. Cl.[7] ............................................... G06F 19/00
(52) U.S. Cl. ............................ 702/32; 702/85; 702/30; 73/23.22; 73/23.23

(58) Field of Search .............................. 702/32, 30, 66, 702/31, 22, 23, 27, 183; 73/23.23, 23.22

(56) References Cited

U.S. PATENT DOCUMENTS

| 3,668,380 A | 6/1972 | Claxton ................. 364/498 X |
| 3,797,300 A | 3/1974 | Sato ......................... 73/23.23 |
| 4,355,533 A | 10/1982 | Muldoon .................. 73/23.23 |
| 4,674,323 A | 6/1987 | Rulf et al. ................. 73/61.52 |
| 4,802,102 A | 1/1989 | Lacey ........................ 364/497 |
| 5,311,444 A | 5/1994 | Ohta .......................... 364/497 |
| 5,442,574 A | 8/1995 | Shinya ................. 364/571.01 |
| 6,076,047 A | 6/2000 | Ito et al. ...................... 702/30 |

FOREIGN PATENT DOCUMENTS

| JP | 6154181 | 11/1986 |
| JP | 6232360 | 2/1987 |
| JP | 6388443 | 4/1988 |
| JP | 694696 | 4/1994 |

Primary Examiner—John Barlow
Assistant Examiner—Hien Vo
(74) Attorney, Agent, or Firm—Kenyon & Kenyon

(57) ABSTRACT

A method of properly correcting a base line. A concept of flexibility of a base line is introduced as an input index and a gravitation is presumed between the base line and signal data which is measured, thereby constructing a method of correcting the base line which changes gentler than a change in signal with respect to time in a peak area and which is sensitive to an area where a value of the signal data is small. A base line like a natural and smooth curve which isn't easily influenced by a local change in signal such as noise or the like can be set by an input of the flexibility.

2 Claims, 19 Drawing Sheets

DETECTING TROUGH PORTION   NOT DETECTING TROUGH PORTION

B: BASE PORTION
V: TROUGH PORTION

IMPROPER STARTING POINT / ENDING POINT OF THE PEAK

PROPER STARTING POINT / ENDING POINT OF THE PEAK

| TIME | FUNCTION | VALUE |
|---|---|---|
| 0.0 | B.L.FLEX | 70 |
| 2.5 | B.L.FLEX | 90 |
| 7.5 | B.L.FLEX | 50 |

| BASELINE VALUE | CORRECTION PERIOD |
|---|---|
| HARD | 0.0 - 2.5 |
| M.HARD | 2.5 - 7.0 |
| MEDIUM | 7.0 - |

——— HARD
------ MEDIUM
—·—·— SOFT

| NAME:NE | UNIT: pg/ml | | N: 10 |
|---|---|---|---|
| FLEX | MEAN | SD | CV(%) |
| HARD | 102.50 | 2.15 | 2.1 |
| MEDIUM | 98.42 | 1.67 | 1.7 |
| SOFT | 98.21 | 2.26 | 2.3 |

| NAME:NE | UNIT: pg/ml | | N: 10 |
|---|---|---|---|
| FLEX | MEAN | SD | CV(%) |
| HARD | 100.14 | 1.70 | 1.7 |
| MEDIUM | 99.21 | 1.59 | 1.6 |
| SOFT | 99.07 | 1.40 | 1.4 | x : PICK UP POINT

DATA PROCESSING APPARATUS FOR CHROMATOGRAPH

This is a continuation of application Ser. No. 10/319,692 filed 16 Dec. 2002, now U.S. Pat. No. 6,675,107, which is a continuation of application Ser. No. 09/940,636 filed 29 Aug. 2001, now U.S. Pat No. 6,529,836, which is a continuation application Ser. No. 09/562,026 filed 1 May 2000, now U.S. Pat. No. 6,314,374, which is a continuation of application Ser. No. 08/605,416 filed 22 Feb. 1996, now U.S. Pat. No. 6,148,266.

BACKGROUND OF THE INVENTION

The present invention relates to a data processing apparatus for a chromatograph and, more particularly, to a method of correcting a base line.

According to Japanese Patent No. 1,385,425 (Japanese Patent Publication No. 61-54181), as a method of correcting a base line of non-separation peaks, there are:

(1) the N method, (2) the θ method, and (3) the method of merely connecting a base portion by a straight line (non-correction method).

In the N method, the number of peaks (N) is designated, N peaks are collected as one peak, and either a base portion or a trough portion is connected by a straight line (FIG. 3(A)). The base portion is a portion that is judged as not a peak area by using a change amount of signal as an index.

In the θ method, an inclination is intentionally loosened when the inclination seems to be too steep in the N method (FIG. 3(B)).

The non-correction method is a most typical method and is effective when the base line is estimated to be like a straight line (FIG. 3C). In addition, there is also a case of correcting a base line by intentionally selecting a forward horizon method (FIG. 3D), a backward horizon method (FIG. 3E), a special processing method of a shoulder peak (FIG. 3F), or the like in accordance with a peak shape of each chromatogram.

Each of the above base line correcting methods has both merits and demerits and is selected depending on a particular case, since it is difficult to unconditionally determine the base line. Although some methods in which the base line is unconditionally determined have been proposed (Japanese Patent Application Laid-Open Sho 62-32360, Japanese Patent Application Laid-Open Sho 63-88443, Japanese Patent Application Laid-Open Hei 6-94696, and the like), those methods are not yet generally used.

In all of the above methods, the base line is corrected on the basis of the base or trough portion existing in the chromatogram.

An algorithm of searching the base or trough portion generally tends to be too sensitive to a local fluctuation in a signal. For example, a case where the trough portion is detected and a case where it is not detected occur depending on a magnitude of noise. A detection of a starting point and an ending point of a peak, that is, an end point detection of the base portion is also disturbed by noise. After all, such a correction of the base line is easily affected by noise and quite different base lines may be obtained due to a slight difference in signals.

By a similar reason; there is a case where the base line largely fluctuates when parameters such as sensitivity, slope, and the like, to detect the base portion or trough portion, are improper.

In the case where the base line is experientially estimated to be horizontal, if a horizontal straight line is applied to the base portion, a proper base line can be obtained. In the case where the base line may possibly not be horizontal, however, a method of obtaining the base line by continuing the base or trough portion with a straight line like a graph of polygonal line is not always proper.

SUMMARY OF THE PRESENT INVENTION

It is an object of the invention to provide a data processing apparatus for a chromatograph, which solves the above problems, forms a stable base line without being affected by a local noise of a chromatogram, and corrects the base line irrespective of local fluctuations of a chromatograph.

In a data processing apparatus for a chromatograph comprising base line determining means for detecting an output value of a detector for a chromatograph obtained with the elapse of time, forming a chromatogram on the basis of the detection result, and determining a base line on the basis of a shape of the chromatogram, when the base line is corrected, a deviation in the direction of the output value between each of forming points which form the base line and a forming point adjacent to the forming point is largely reduced as the deviation becomes larger.

Adjusting means of the base line adjusts so as to reduce a change amount of the deviation proportional to the deviation with an increase in the deviation and to increase the change amount of the deviation proportional to the deviation with a decrease in the deviation.

Further, an adjusting range of the adjusting means from a base line is determined on the basis of the shape of the chromatogram to a linear base line connecting base lines before and after a time zone in which the chromatogram appears as a measuring target appears.

There is also provided selecting means for applying the above construction to an optional time zone of the measurer.

In the time zone in which the chromatogram appears as a measuring target sample, the deciding means for deciding the base line on the basis of the shape of the chromatogram decides the base line on the basis of a distance on the same time base from either one of a straight line connecting a starting point and an ending point of the time zone in which the chromatogram appears, a straight line connecting the starting point and the trough portion of the chromatogram, and a straight line connecting the ending point and the trough portion of the chromatogram to the chromatogram, and arranges a forming point of the base line so as to shorten a distance on the same time base from the straight line for the distance to the base line with an increase in the foregoing distance.

In one mode of the arrangement of forming points on the base line, the base line is set to the same line as the chromatogram in the time zone in which the foregoing distance is equal to a value which ranges from zero to a predetermined value.

The base line of the chromatogram inherently has a very loose change as compared with the signal change in the peak area and its change width is narrow.

That is, when the base line is regarded as a collection of a plurality of points, it is considered that two neighboring points among the points are loosely bound to each other. Namely, a base line of a shape having a local projection is impossible. If the base line having a local projection is drawn, it is considered that the portion is projected due to improper drawing means of the base line or an influence by noise occurring somewhere in a chromatograph device.

In consideration of the above, when the base line drawn by various means is regarded as one line constructed by a plurality of points, the correction is performed so as to reduce a deviation in the direction of the output value between the two adjacent points among the points as the deviation becomes large, so that the base line adapted to the above condition can be drawn.

The base line drawn as mentioned above can be adjusted while maintaining a gentle line in a manner such that when the deviation between the two points in a time zone is increased, a change amount of the deviation is reduced in proportion to the increase in the deviation and, when the deviation is reduced, the change amount of the deviation is increased in proportion to the decrease in the deviation.

Another characteristic of the base line is such that the base line is strongly attracted to an area in which a signal value expressed by the chromatogram is small.

It is because the signal value that is caused by another component which is a factor of the noise is unlikely to appear in the time zone in which a target component appears and an output value which is not so large is generated since it corresponds to an amount of noise after all, and the like.

In consideration of the above, the base line corresponding to the above characteristic can be drawn by arranging the forming points of the base line in a manner such that as the distance in the time base direction from the chromatogram to the base line as a reference (linear base line connecting base lines before and after the time zone in which the chromatogram as a measuring target appears) becomes longer, a distance in the same time zone from the straight line for the foregoing distance to the base line is largely reduced.

When the drawing means of the base line and the correcting means of the base line are used together, since the projected portion of the base line drawn by the drawing means can be corrected by the correcting means of the base line, the correction of the base line in which the two characteristics of the base line are considered can be performed.

BRIEF DESCRIPTION OF THE DRAWINGS

FIG. 14 is a diagram of an output example showing reproducibility of a quantitative value;

FIG. 15 is a flowchart showing a condition setting for a base line correction before a signal is taken in;

FIG. 16 is a flowchart showing a condition setting for the base line correction after a signal is taken in;

DETAILED DESCRIPTION

Figure 4:
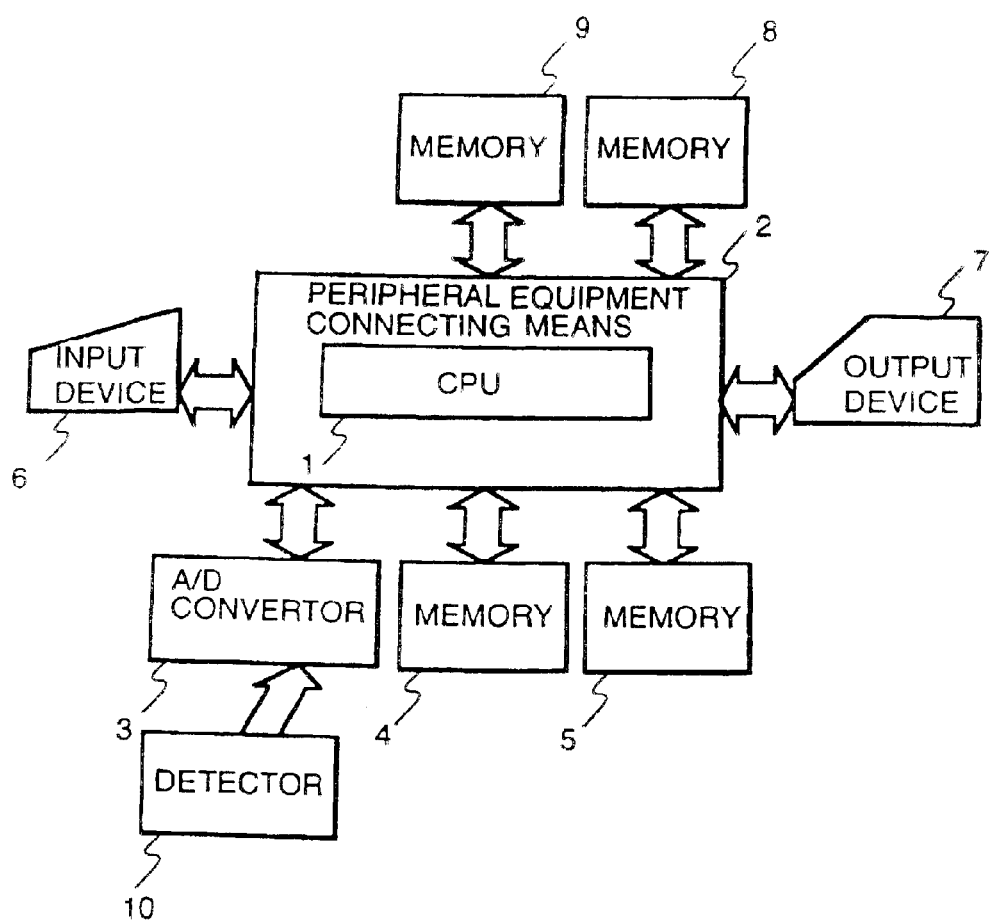
FIG. 4 is a diagram showing a construction of a data processing apparatus according to an embodiment of the invention.

An embodiment of the invention will be described hereinbelow with reference to FIG. 4. FIG. 4 is a block diagram of a data processing apparatus for a chromatograph to which the invention is applied. In FIG. 4, reference numeral 1 denotes a central processing unit (CPU); 2 a peripheral equipment connecting unit; 3 an A/D converter; 4 a signal data memory; 5 a control command memory; 6 an input device; 7 an output device; 8 a result data memory; 9 a process parameter memory; and 10 a detector for a chromatograph.

An analog signal from the detector 10 for a chromatograph is converted to a digital signal by the A/D converter 3 and is supplied to the CPU 1 through the peripheral equipment connecting unit 2. By a command in the control command memory 5, the signal is converted to signal data of a predetermined format and the data is stored into the signal data memory 4.

An embodiment of forming means of a base line of a chromatogram and correcting means of the base line of the formed chromatogram of the invention will now be described.

According to the embodiment, the base line is formed and corrected on the basis of two characteristics of the base line of the chromatogram. The two characteristics are such that the base line is strongly attracted to an area in which a signal value expressed by the chromatogram is small and that neighboring points in the base line formed by continuous points are loosely bound.

The former characteristic is coped with in a manner such that as a distance between each of continuous points which form the chromatogram and a forming point of a reference base line (in the embodiment, a line obtained by connecting base lines before and after a time zone in which a peak of a measuring target sample appears) in the same time base direction becomes large, a ratio of length between the straight line for the distance and the forming point of the base line is reduced.

That is, as the reference base line on the same time base becomes closer to the chromatogram, the reference base line is strongly attracted to the chromatogram. It can be defined that gravitation or magnetism acts between the chromatogram and the reference base line on the same time base from this point of view, since when the distance is long, only a weak force acts, and when the distance is short, a strong force acts.

The latter characteristic is coped with in a manner such that the longer a distance in the time base direction between the adjacent points among the continuous points which form the base line is, the more the distance is reduced.

When a physical idea is adapted to the above, the characteristic of spring can be considered since the more a spring is stretched, the stronger a force acts.

A formation of the base line in consideration of the two characteristics of the base line will now be considered.

Figure 1:
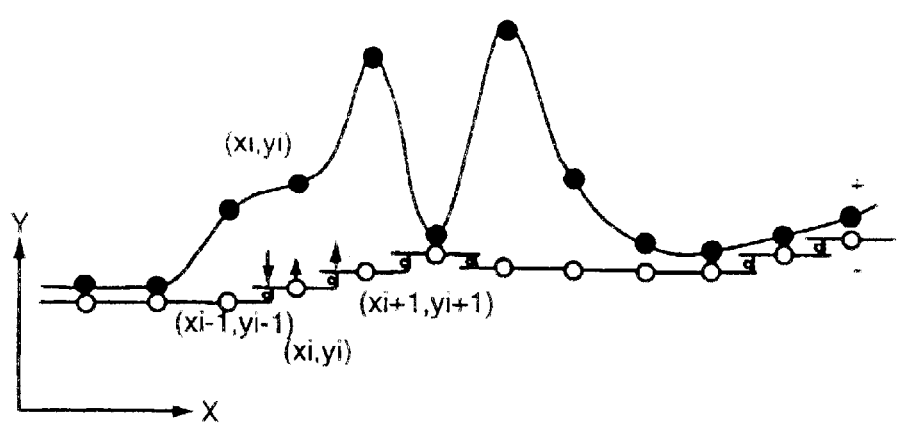
FIG. 1 is a diagram showing an example of a physical model of the invention.
Figure 2A:
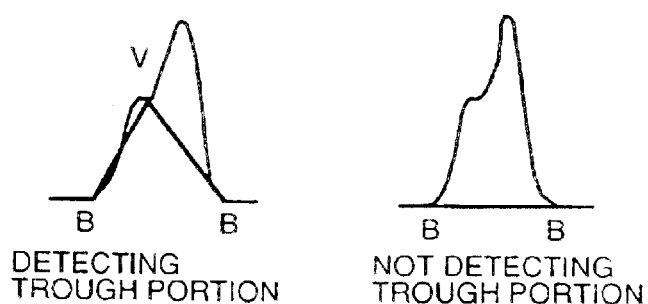
FIGS. 2A–2B are diagrams showing problems of a conventional method.
Figure 2B:
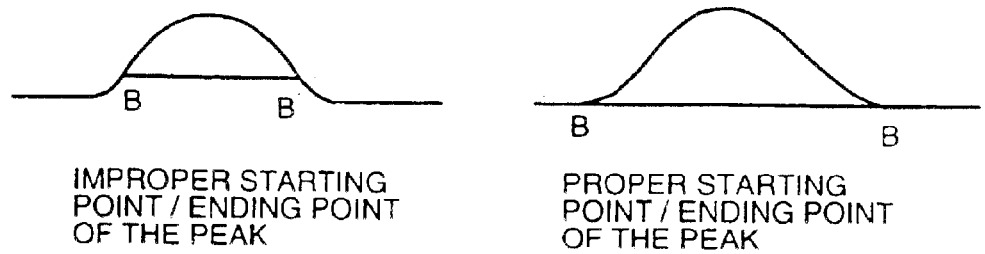
Figure 3A:
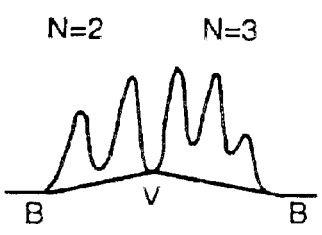
FIGS. 3A–3F are diagrams showing a conventional method of correcting a base line.
Figure 3B:
Figure 3C:
Figure 3D:
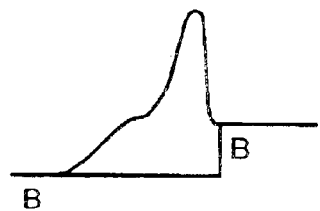
Figure 3E:
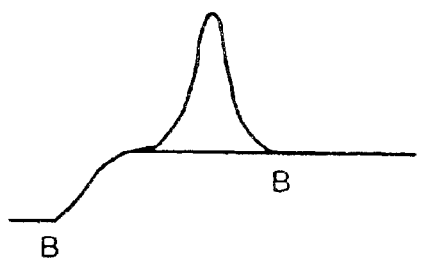
Figure 3F:
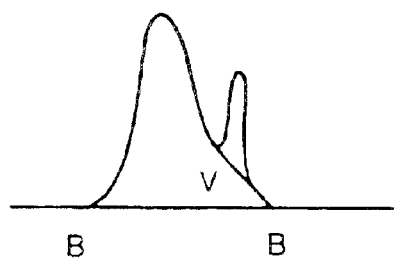

FIG. 1 is a diagram showing a specific physical image considering the two characteristics. Although a two-dimensional elastic body (spline) or plastic body (adjustable ruler) or the like can be introduced as a base line, the formation of the base line is considered here in a category of dynamics of a one-dimensional elastic body, particularly, statics in which a balance of forces used for simplicity of explanation.

A signal waveform doesn't move and points each having plus charges are fixed at equal intervals. Particles having minus charges are arranged on the base line so as to correspond to the plus charges. It is now assumed that a Coulomb force acts only between the plus and minus charges on the same x-coordinate. The particles of minus charges cannot freely move and the neighboring particles are connected by a spring. A model wherein two or three neighboring particles are weighted and connected by a spring is also possible. It is also assumed that elasticity of the spring works only in the vertical direction (Y direction). That is, axes attached to blank circles in FIG. 1 move only in the vertical direction and don't rotate.

The straight base line is horizontally lifted from the lower part of signal data. The straight line is rotated by using a point which is contacted for the first time as an axis and a point to be contacted next is obtained. The straight line is rotated right and left and a contact point which is located further from the axis is used. A gravitation is acted in this instance and the base line is allowed to be curved. The signal data and the base line make contact at a point where the gravitation acts more than the elasticity of spring which acts against to be curved.

Expression 1 shown below is a balance equation of force on an optional x-coordinate.

balance equation of force:

$$K \frac{q^2}{(Y_i - y_i)^2} - k(y_i - y_{i-1}) - k(y_i - y_{i+1}) = 0 \qquad \text{[expression 1]}$$

where,
K: constant of Coulomb force
$Y_i$: (i)th signal data point (constant)
q: charge (constant)
$y_i$: (i)th base line point (variable)
k: spring constant The condition is $Y_i \geq y_i$. When $Y_i = y_i$, the balance equation is unnecessary.

$Y_{i-1}, Y_i, Y_{i+1}$, and the like are variables and the others are constants. A point where an actual signal value $Y_j$ and a base line $y_j$ are equal, namely, a point of contact is eliminated from the balance equation and the number of equations is set to n. Although n variables can be obtained from the n balance equations, it is more efficient to solve the equation by approximating it to a linear equation such as $Y_i$ or the like as shown below. When $Y_i \gg y_i$:

$$\frac{Kq^2}{Y_i^2}\left(1 + \frac{2y_i}{Y_i}\right) - k(y_i - y_{i-1}) - k(y_i - y_{i+1}) = 0 \qquad \text{[expression 2]}$$

The base line obtained as mentioned above is shown by blank dots in FIG. 1. Although the number of dots expressed is small in FIG. 1, a calculation is actually performed by using all of the sampling points. By correcting the base line with such a model, the base line isn't excessively curved and the base line which is properly contacted and close to a portion where the signal value is small can be obtained. That is, flexibility of the base line is characterized by parameters of strength of materials such as spring constants and the like, thereby preventing a rapid local change. The signal data and the base line are attracted by a gravitation force having a distance dependency such as the Coulomb force or the like, so that the base line can be brought especially strongly close to an area where the value of the signal data is small.

In case of actually properly correcting the base line by data processing apparatus, an index such as strength of flexibility is input as a parameter like the spring constant and a distance dependency of gravitation (inverse-square type, exponential function type, step function type, and the like) is designated.

Although the base line has been formed and corrected on the basis of the two characteristics of base line in the illustrated embodiment, the base line can also be formed and corrected by taking account of only one of the two characteristics.

That is, it is also possible to form the base line by base line forming means as in the conventional technique, input the index of strength of the flexibility, such as spring constant, as a parameter, according to the invention, smooth a projected portion in the base line obtained by using the base line forming means which depends on the distance between the chromatogram and the reference base line of the invention, and the like.

Various concepts can be included in the base line correction according to the embodiment of the invention as mentioned above. Selecting means will now be described in accordance with the order of steps of the base line correction.

Figures 14, 15:
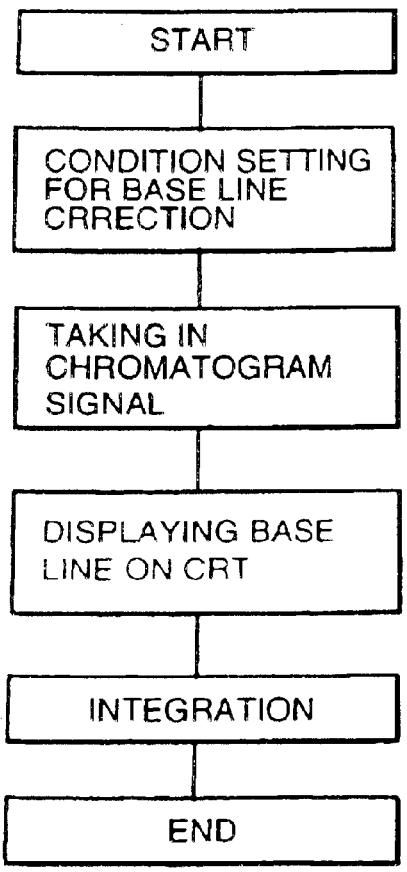
Figure 16:
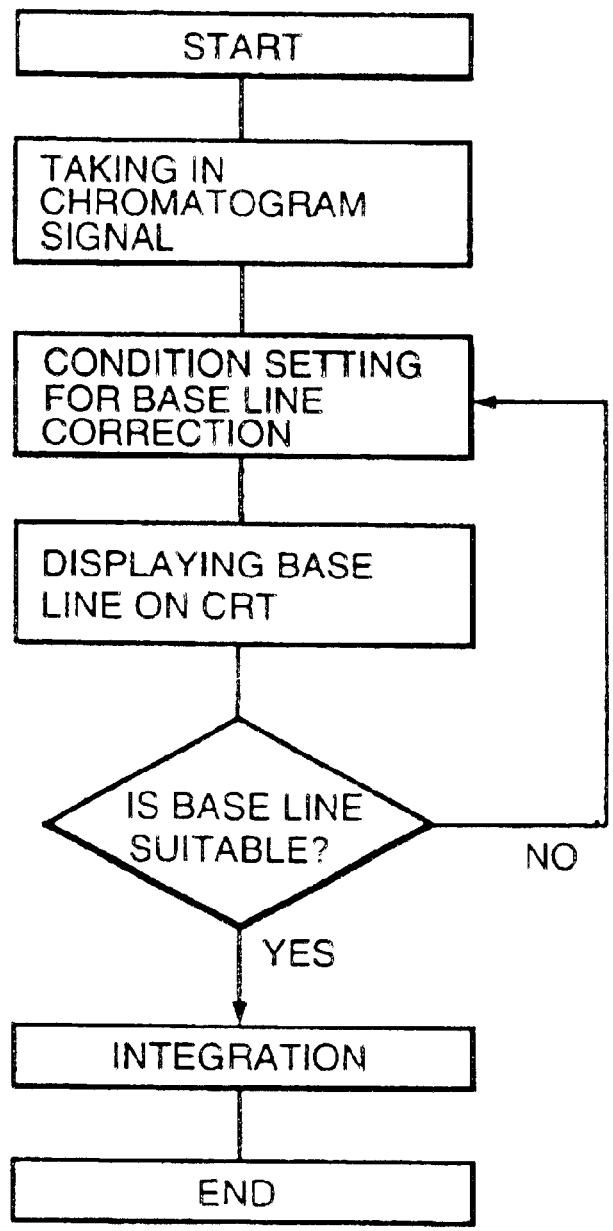

Parameters for the base line correction have preliminarily been stored into the process parameter memory 9 from the input device 6 before a signal is taken in (FIG. 15). The following inputting operation will be also similarly executed in a case of again performing the base line correction to the signal data once taken in (FIG. 16).

Figure 6:
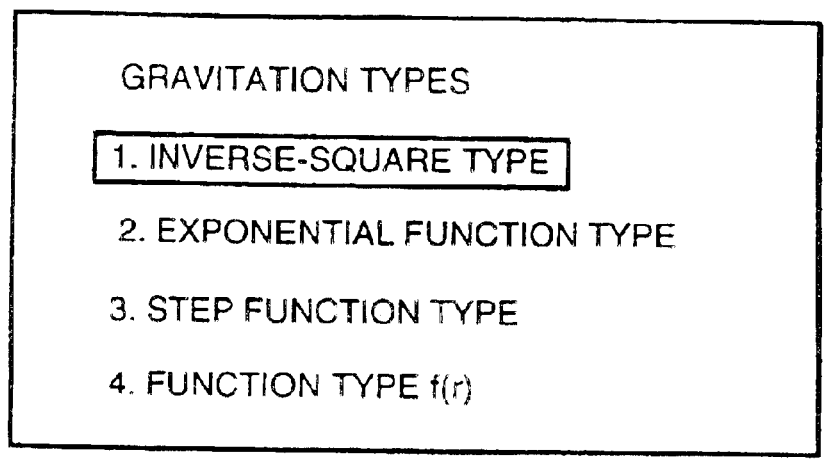
FIG. 6 shows an input screen of gravitation types.
Figure 17:
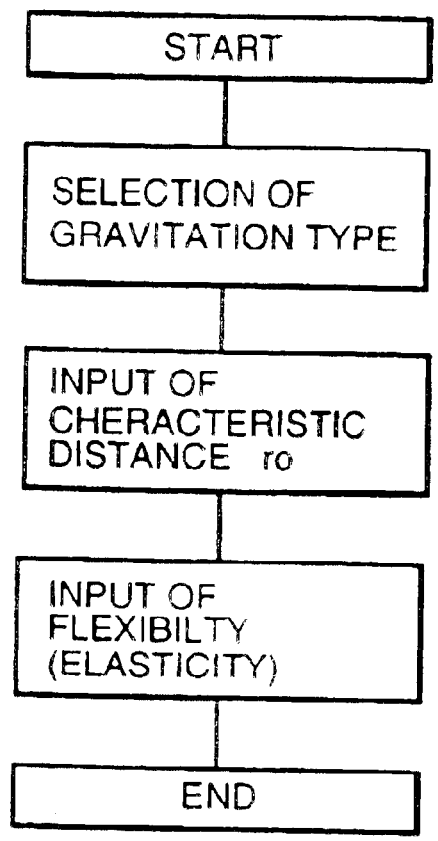
FIG. 17 is a flowchart 1 showing a condition setting for the base line correction.

The type of gravitation is selected from another picture screen (FIGS. 6 and 17). Although a parameter of a gravitation constant has to be inherently set, the input can be omitted since it is in relative relation to the flexibility of the base line. Parameters regarding a distance (pV) between the signal data and the base line have to be input. A characteristic distance ro is directly input by a numerical value ($\mu$V) or can also be automatically set by a peak height, a value that is constant times as large as noise, or the like.

The inverse-square type gravitation relates to an interaction generally existing in the natural world such as Coulomb force, gravitation, or the like and has the shape of expression 3, as shown below. The exponential function type gravitation is expressed by expression 4 as shown below and when the distance becomes long, the gravitation rapidly attenuates as compared with that of the inverse-square type.

$$f(r) = \frac{1}{r^2} \qquad \text{[expression 3]}$$

$$f(r) = e^{-r/r-0} \sim \begin{cases} 1 - \dfrac{r}{r_0} & (r << r_0) \\ 0 & (r << r_0) \end{cases} \qquad \text{[expression 4]}$$

Figure 7:
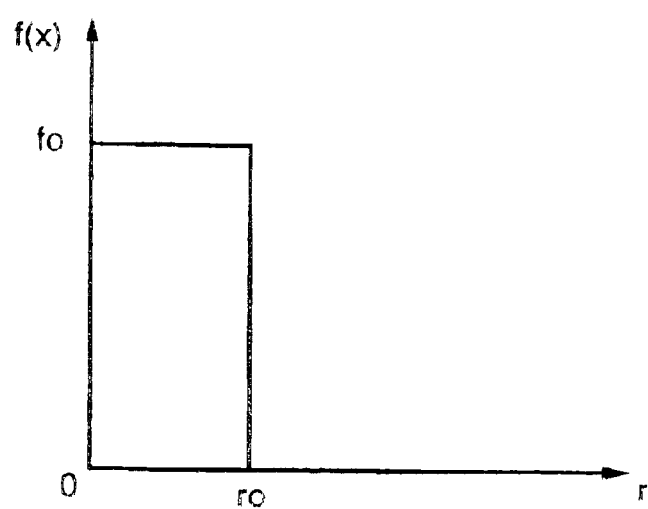
FIG. 7 shows a profile of a gravitation of a step function type.

It is necessary to input a parameter of a distance $r_0$ ($[(\mu$V). The step function type gravitation is expressed by a profile of a gravitation as shown in FIG. 7. When the distance between the signal data and base line becomes shorter than the distance r0, the gravitation works. Since the presence or absence of the gravitation is decided only by judging the distance ($\mu$V), there is an advantage such that a calculating process can be omitted. An optional expression can be inputted to the function type and a function which becomes smaller as the distance becomes longer such as expression 5 shown below or the like can be used.

$$f(r) = \frac{1}{r} \qquad \text{[expression 5]}$$

Figure 5A:
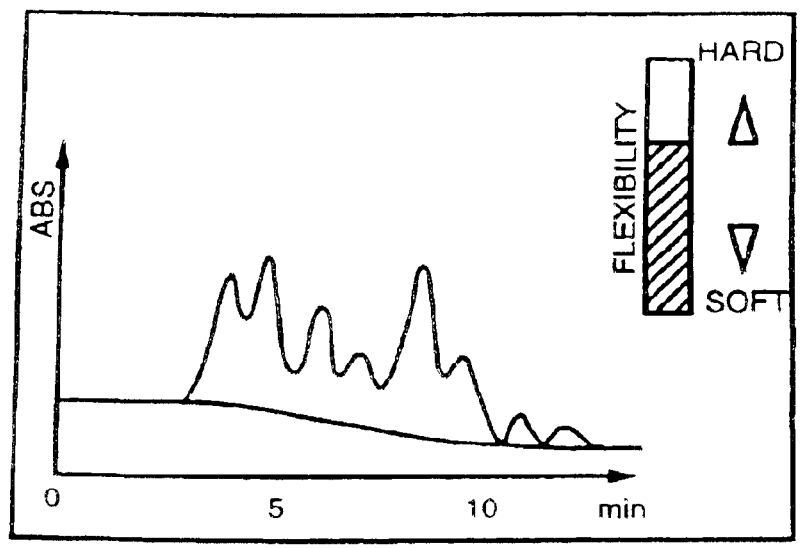
FIGS. 5A–5B are diagrams showing output examples of a chromatogram.
Figure 18:
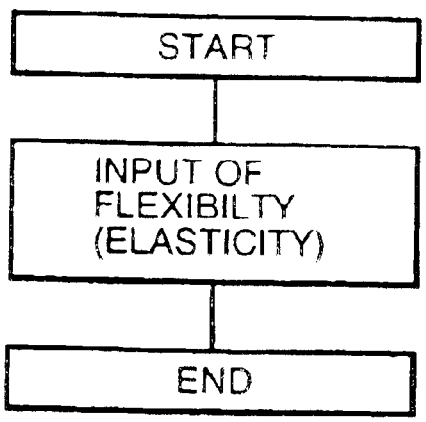
FIG. 18 is a flowchart 2 showing a condition setting for the base line correction.

The flexibility of the base line is set by using the CRT output device 7 from the keyboard input device 6 as shown in FIG. 5A. Hardness can be adjusted by a cursor key while watching a flexibility bar graph (FIG. 18) or the hardness can be also picked up on the CRT. The setting can be changed by the cursor key to select a proper base line even after the signal is taken in. Since a medium hard base line is set here, a base line which is like a straight line is obtained.

From a point of view of strength of materials, the flexibility of the base line corresponds to a spring constant or a Young's modulus. Actually, the relative elasticity intensity from 0 to 100 is input. When 0 is input, the spring loses the elasticity and becomes like a string and the base line becomes quite the same as the waveform of the signal data. When 100 or infinity is input, the base line becomes like a stick of a rigid body having a high rigidity or a straight line which contacts the signal line with at least two points.

Figure 5B:
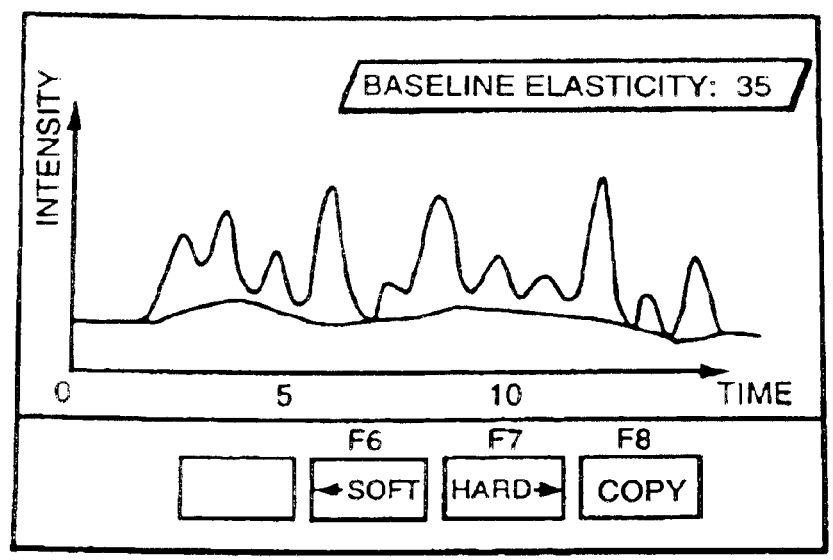

In FIG. 5B, baseline elasticity is input by a numerical value from a SOFT key. Since a rather soft base line is set, the base line is more curved. The chromatogram and a calculation result is sent to the printer output device 7 to be printed using a COPY key.

In addition to use of the spring constant as a parameter of flexibility, a correction which minimizes a distortion energy of the base line like an adjustable ruler, a correction like a spline (bar flexibility ruler) which minimizes a whole curve, and the like can be also adapted.

Figure 12:
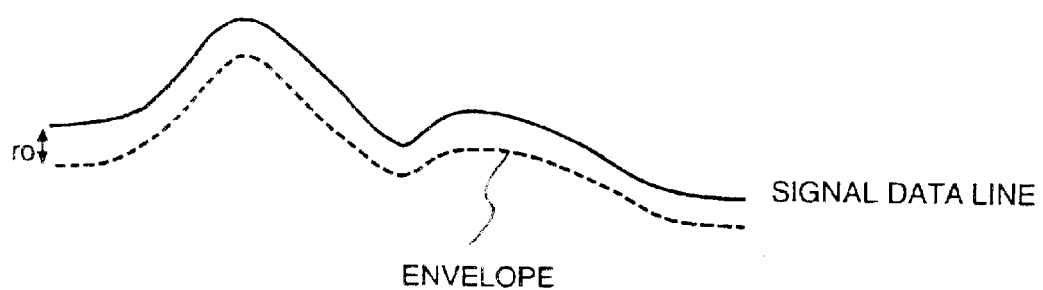
FIG. 12 is an explanatory diagram of a base line envelope method.
Figure 19:
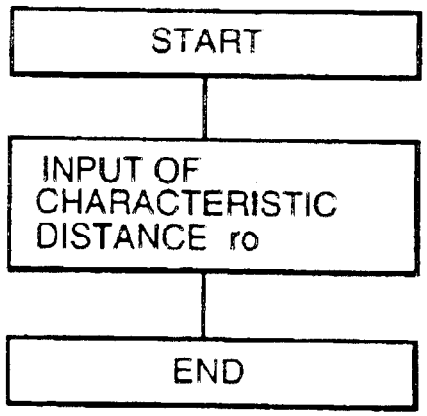
FIG. 19 is a flowchart 3 showing a condition setting for the base line correction.

As a derivative method of the step function type gravitation, a base line envelope method can be considered. An envelope (envelope band) of the distance $r_0$ is provided above and below the flexible base line. When the signal data exists in the envelope, the base line contacts the data line, or as shown in FIG. 12, when there is an envelope below the signal line, the base line is contacted from the lower part. Such operations are sequentially repeated, thereby determining the shape of the base line. In the method, it is also necessary to input the parameters regarding the distance $r_0$ ($\mu$V) in a manner similar to the step function type (FIG. 19). This can be regarded as a special case where f0 is equal to infinity in the step function type of FIG. 7. Or, this is almost the same as a method where an interval in which the change amount of a signal is small is regarded as a base portion and a shape which is decided when the flexible base line is contacted from the lower part to the base portion is set to the base line. Further, when the elasticity is set to 0, the base line becomes like a string, a portion which is not contacted to the data line becomes a straight line as if the conventional non-correction method is used.

As another base line forming means, the base line envelope means shown in FIG. 29 can be also considered.

Figure 29A:
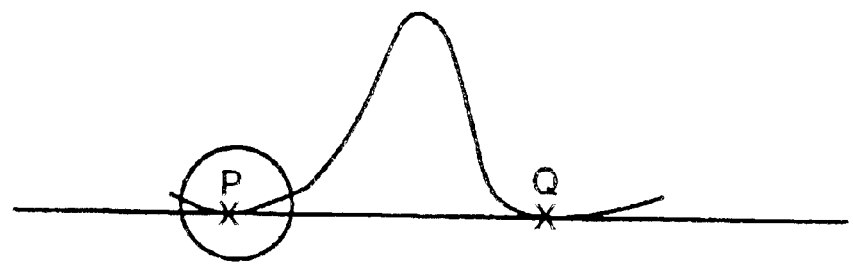
FIGS. 29A–29D are explanatory diagrams of a second base line envelope method.
Figure 29B:
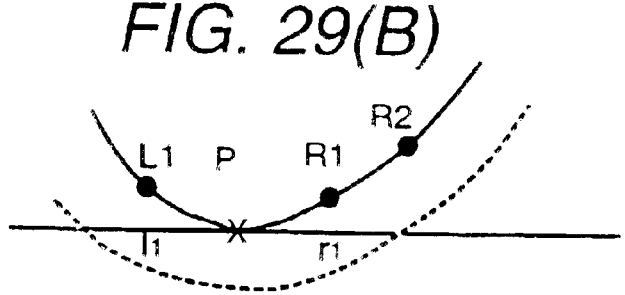
Figure 29C:
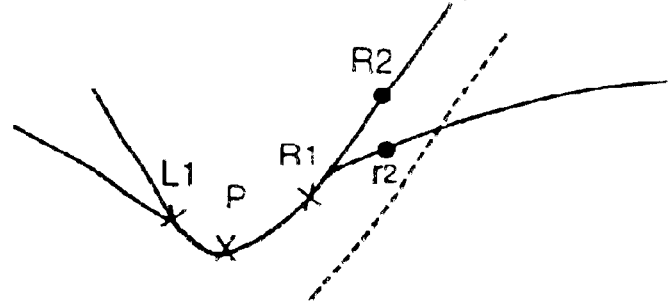
Figure 29D:
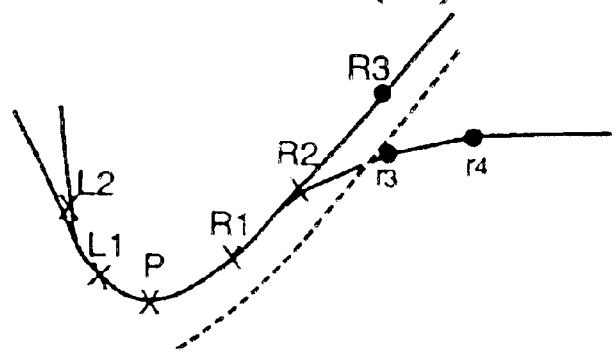

As shown in FIG. 29A, a straight line is contacted to the chromatogram from the lower part with two points (P) and (Q). An envelope line of dotted line is shown on an enlarged diagram of the (P) point in FIG. 29B, points $r_1$, $r_2$, and 11 on a time base corresponding to points R1, R2, and L1 on the chromatogram are contacted to the points R1, R2, and L1 on the chromatogram in accordance with the order of FIGS. 29(C) and 29(D) and the contacting operation is stopped when a point as shown by a point r3 which is deviated from the envelope line appears. The above operation is similarly applied to the (Q) point and the base line between the (Q) and (P) points is curvedly modified in accordance with a vector of the base line having a point contacting the chromatogram, thereby enabling a smooth shaped base line to be drawn.

Advantages of the base line correcting method which is not based on the base portion or the trough portion will be described by using the chromatogram of glycohemoglobin of FIG. 8 as an example. Hitherto, in order to correct the base line so that it contacts a trough portion between s-Alc and A0, the former six peaks have to be collected in the N method. In actual samples, however, there are not always six peaks. It can happen that a trough portion between Ala1 and Ala2 doesn't appear, an F peak disappears, a trough between 1-Alc and s-Alc is not clear, and the like. Due to this, after taking in the signal data, the number of peaks has to be counted again and the N value has to be set again in an offline post-process. According to the present method, by merely setting the flexibility to a proper value, a similar base line can be always obtained irrespective of the number of peaks.

Figures 8, 9A, 9B:
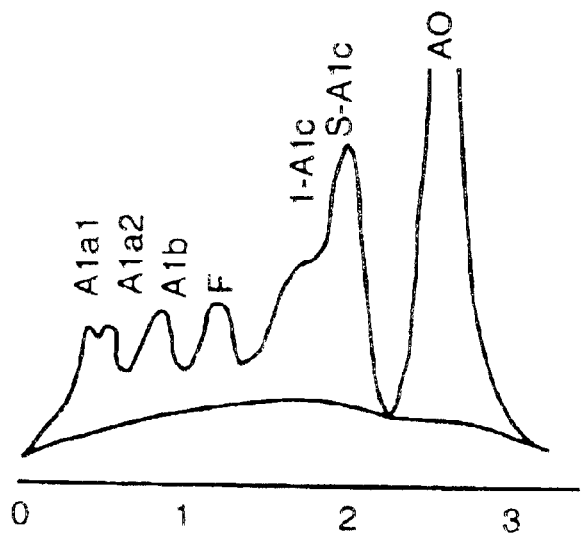
FIG. 8 is an explanatory diagram of advantages of the embodiment of the invention.
FIGS. 9A–9B are diagrams showing an example of a time program of flexibility.
Figure 20:
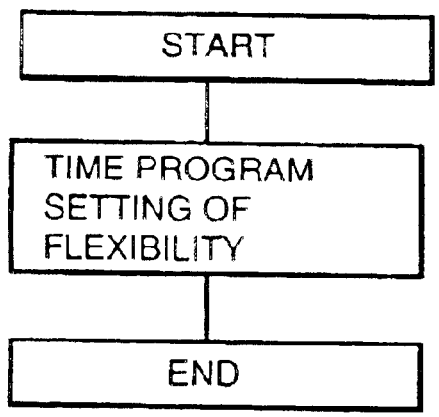
FIG. 20 is a flowchart 4 showing a condition setting for the base line correction.

When the flexibility of the base line is desired to be changed in the middle of the chromatogram, it is set by a time program as shown in FIG. 9A (FIG. 20). When the flexibility of the base line is input as 70 at time 0.0 minute and 90 at time 2.5 minutes, the flexibility can be changed in the interval in a linear gradient manner. A setting can be also performed by subsequently picking up a starting point of the time program and an intensity of flexibility while watching the chromatogram on the CRT.

The flexibility can be also input for an interval by exclusive-use input items for the base line correction as shown in FIG. 9B. HARD is set for a period of time from 0.0 to 2.5 minutes and MEDIUM HARD is set for a period of time from 2.5 to 7.0 minutes. In this case, although a stepwise switching is performed, it is necessary to locally perform a gradient switching at a switching point of 2.5 minutes so as not to have an unnatural curve. As it will be understood from this, one value to designate the flexibility for the whole chromatogram is preferable.

Figure 21:
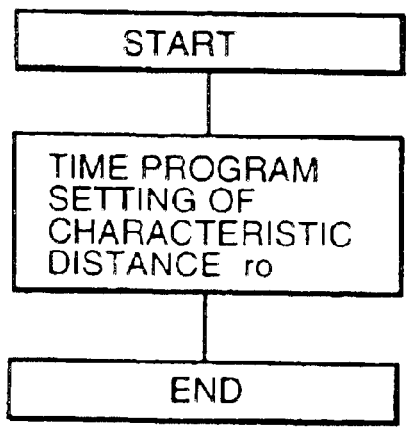
FIG. 21 is a flowchart 5 showing a condition setting for the base line correction.

Similarly, the characteristic distance $r_0$ can be also set by the time program (FIG. 21).

Figure 10:
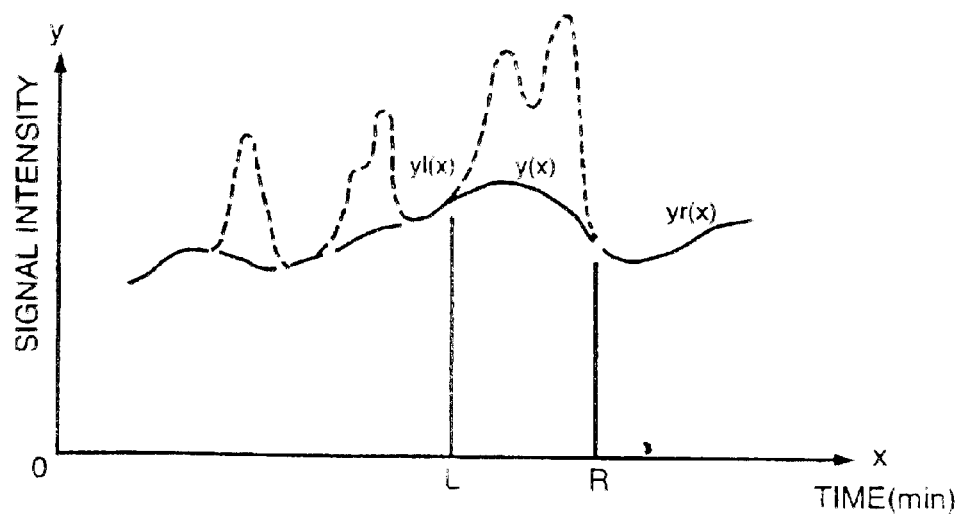
FIG. 10 is a diagram showing an example of a connection of base portions.
Figure 22:
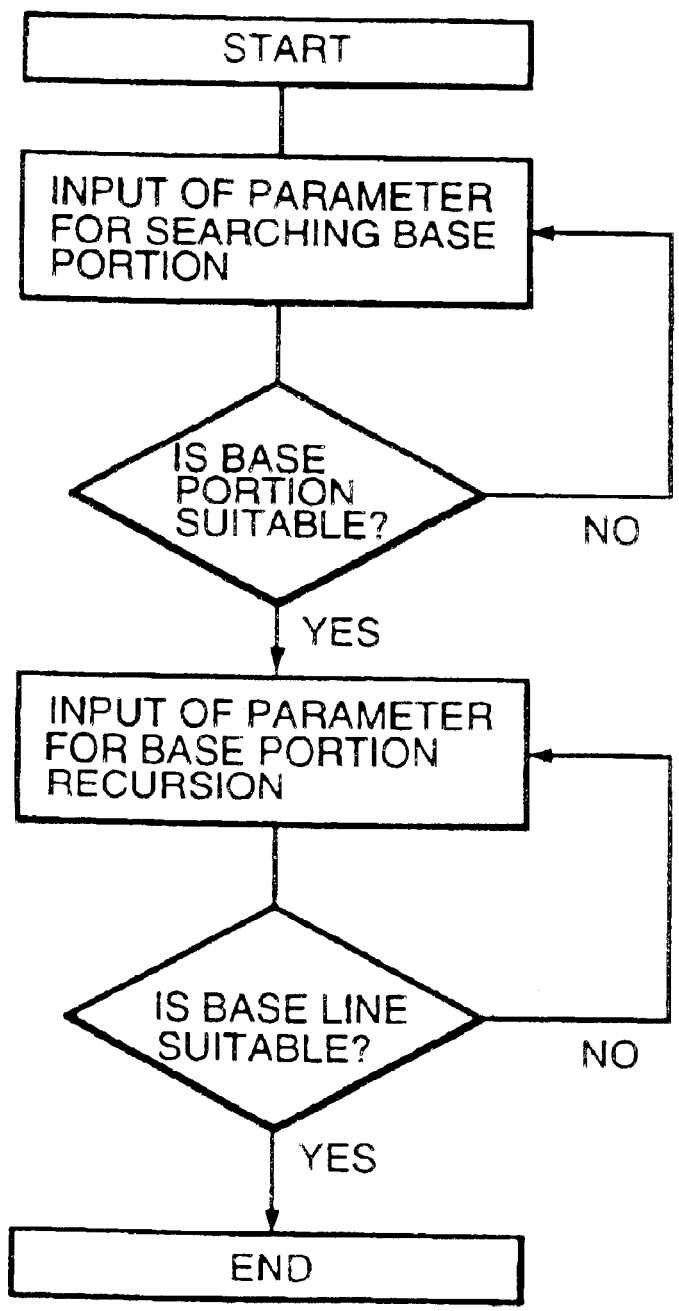
FIG. 22 is a flowchart 6 showing a condition setting for the base line correction.

As another embodiment of the invention, a method of detecting a base portion and connecting the base portion by a smooth curve will be described (FIG. 22). An interval in which the signal change amount is small is searched as a base portion by using parameters such as noise, sensitivity, slope, and the like. FIG. 10 shows a graph made from the base portions obtained as mentioned above.

Instead of the conventional method of detecting the base portion on the basis of the signal amount change as mentioned above, a base portion decided from the relation of gravitation acting between the flexible base line and the signal data line can also be used. A portion where the signal data line and the base line contact in the foregoing embodiment is regarded as a base portion (FIG. 5). Portions which are not contacted are cut, the base portions are left, and a next connecting process follows.

In a manner similar to the foregoing base line envelope method, the flexible base line is contacted to the base portion from the lower part, thereby connecting the base portion. A point such that there is the process exclusively used for searching the base portion in this case is different from the foregoing base line envelope method. There are difficulties such that when the rigidity of the base line is too high, an unnaturally curved base line is obtained. When the elasticity is set to be low, the base portion is connected more linearly, and a smoothness cannot be obtained.

A spline interpolating method is effective to a connection of the base portion. In a general spline method, data points are smoothly connected by using a cubic polynomial. Since this case relates to the connection of the base portion comprising a plurality of points, the process is slightly different. The base portion is regressed by a linear, quadratic, or cubic expression. The quadratic expression is preferable. When the regression isn't successfully performed, points on the connection side of the base portion are used to regress to the quadratic expression. A cubic polynomial for interpolation is determined so that 0th and first derivatives are equal at an end point on the connection side of the base portion.

As shown below, an interpolation expression has four unknown letters, a, b, c, and d. When a regression expression $y_i(x)$ (expression 7) of the base portion on the left side and an interpolation cubic polynomial y(x) (expression 6) make the 0th and $1^{st}$ derivatives equal at an end point L and a similar condition (expression 8) is also requested with respect to the right side, four expressions are obtained and all of the unknown letters can be determined. The connection conditions in this instance for the left-side and right-side regression expressions are shown hereinafter (expression 9).

interpolation cubic polynomial $$y(x)=a+bx+cx^2+dx^3 \qquad \text{[expression 6]}$$

left-side regression expression $$y_l(x)=a_1+b_1x+c_1x^2 \qquad \text{[expression 7]}$$

right-side regression expression $$y_r(x)=a_r+b_rx+c_rx^2 \qquad \text{[expression 8]}$$

conditions of connection $$\begin{cases} y_l(L)=y(L) \\ y_{l'}(L)=y'(L) \end{cases} \begin{cases} y(R)=y_r(R) \\ y'(R)=y_{r'}(R) \end{cases} \qquad \text{[expression 9]}$$

The connection of the base portion can be consequently performed by the spline interpolation method.

Figure 11:
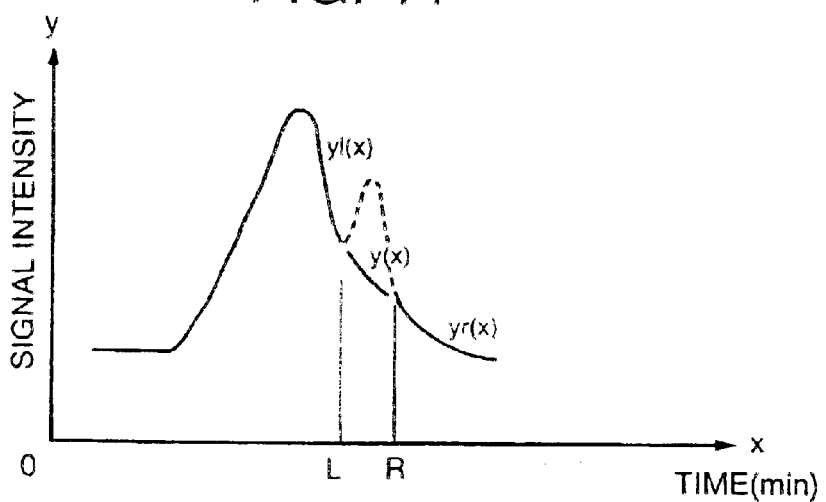
FIG. 11 is a diagram showing an example of a separation of a shoulder peak.

As another embodiment, a case of the shoulder peak will be described. The spline interpolation method is also used in principle in the case. As shown in FIG. 11, the right and left regression expression of the shoulder peak are smoothly connected by the interpolation expression, thereby enabling a parent peak and the shoulder peak to be separated. In this case, a starting point of the shoulder peak is a trough portion and an ending point is, for the convenience, a point of contact when a tangent line is drawn from the trough portion to a foot portion of the parent peak.

Figure 26:
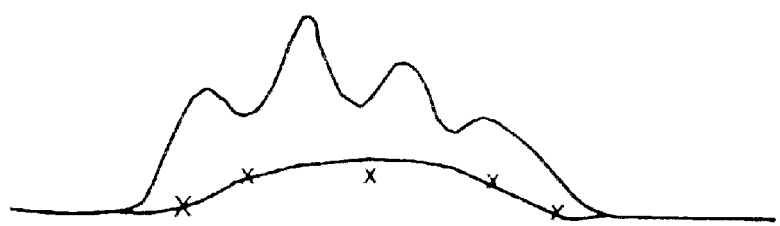
FIG. 26 is a diagram showing a manual pick up method.
Figure 27:
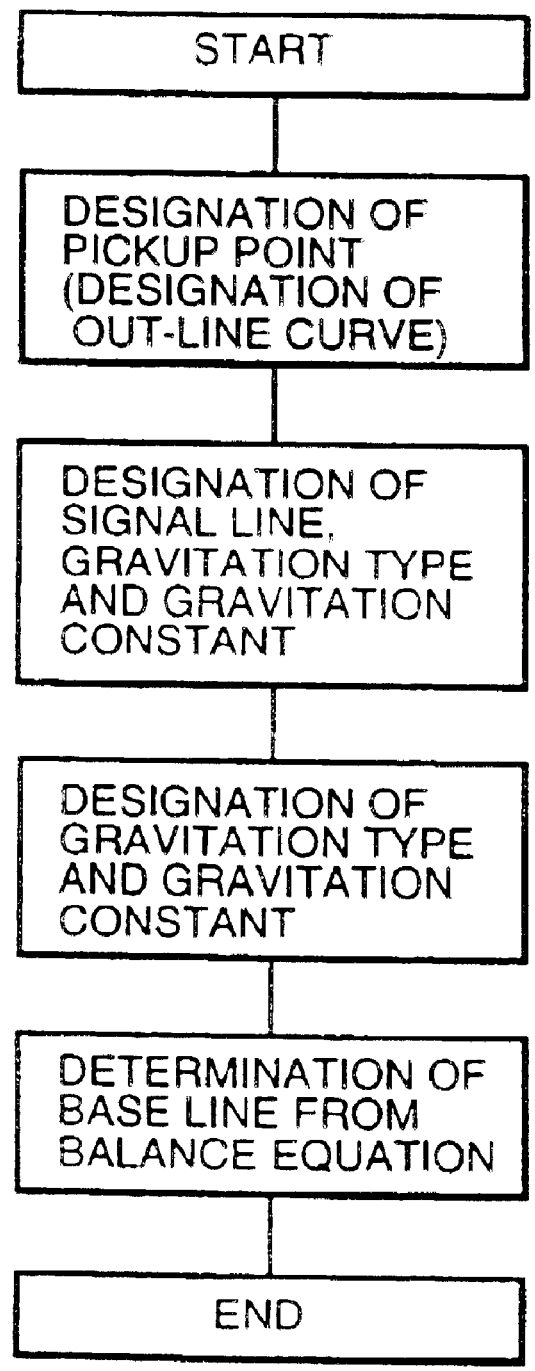
FIG. 27 is a flowchart 1 showing the manual pick up method.

As a last embodiment, a method of manually correcting the base line will be described. A point where a base line is likely to exist is picked up while watching the chromatogram on the CRT (FIG. 26). Although a method of spline interpolating the picked point can also be considered, the method depends on the picked point too much. A method of using the flexible base line is also effective (FIG. 27). In this case, the gravitation is allowed to act downward from the data line to the base line and the gravitation is also allowed to act in the vertical direction between the picked point and the base line. Since it is preferable that the base line and the picked point don't largely separate, the gravitation of a type which acts stronger as the interval between them becomes longer is selected. For example, a gravitation which is proportional to an absolute value of $r^2$ or r is suitable. In this case, an input of a gravitation constant is necessary. The two kinds of gravitations and flexibility are considered and the balance equation is solved, thereby determining the optimum flexibility. Consequently, the base line which is imaged by the operator can be obtained. According to such a method, the correction can be similarly performed even when a curve like an outline is input.

Figure 13:
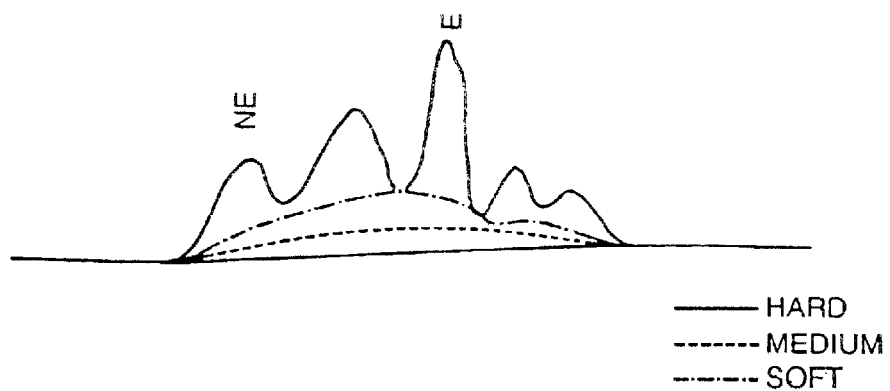
FIG. 13 is a diagram showing an overlay of a base line.
Figure 23:
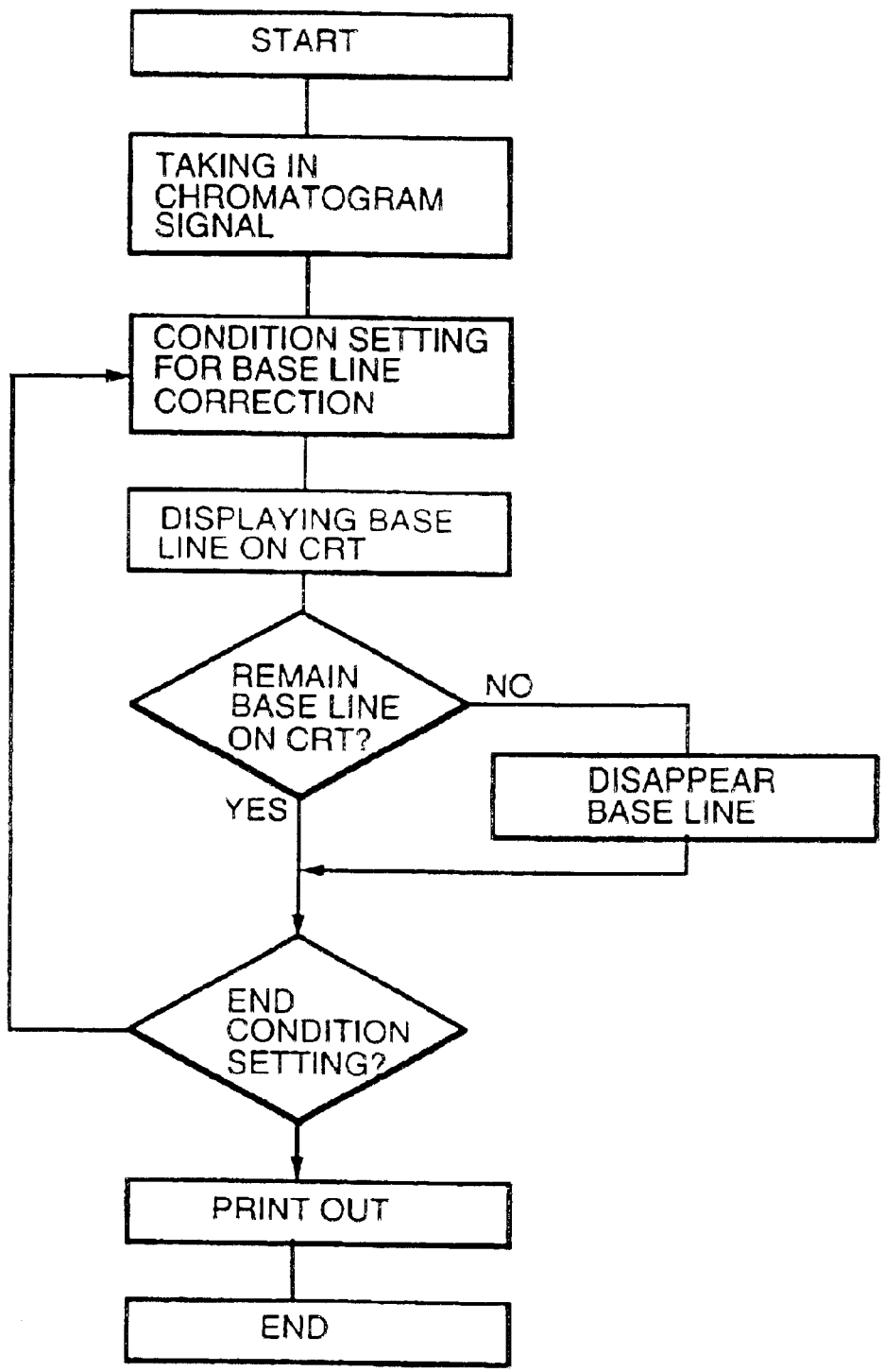
FIG. 23 is a flowchart 1 showing an over display of a base line.
Figure 24:
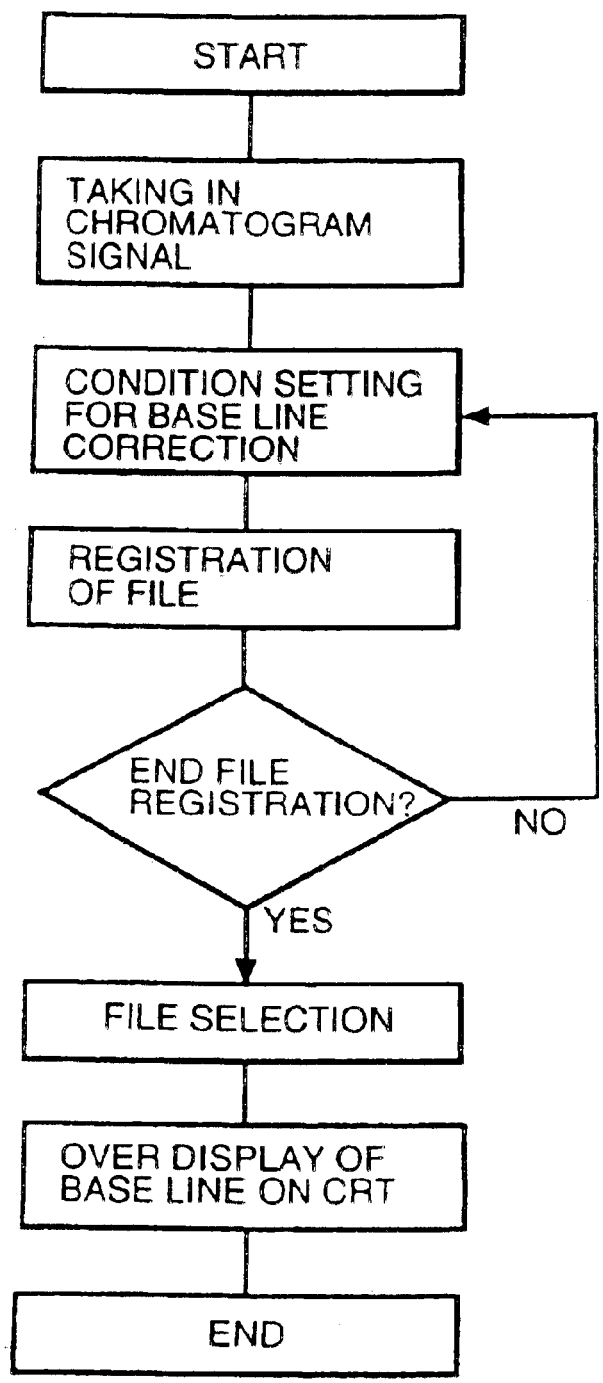
FIG. 24 is a flowchart 2 showing an over display of a base line.
Figure 25:
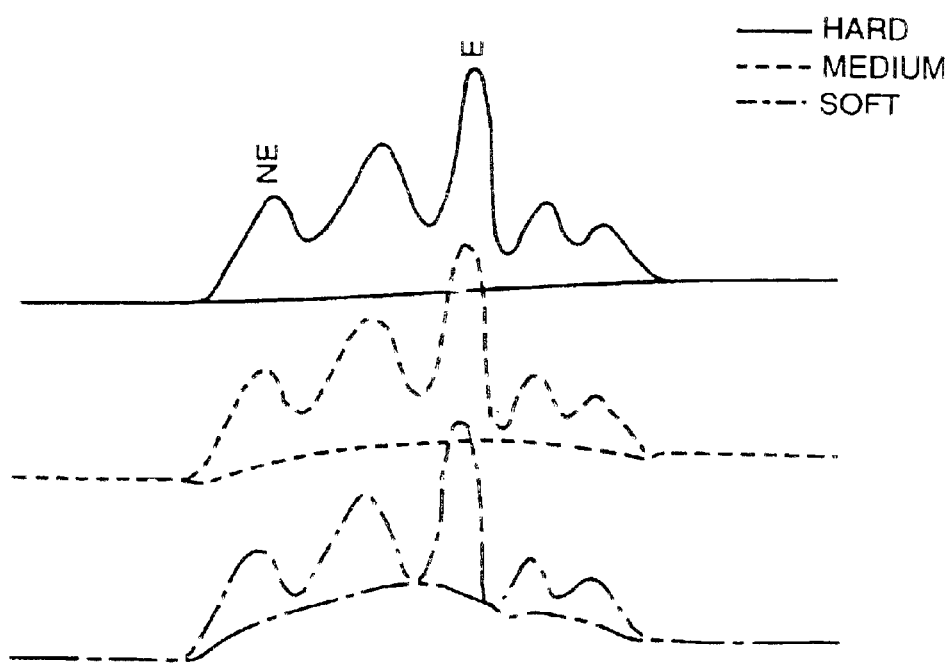
FIG. 25 is a diagram showing an overlay of the chromatogram.
Figure 28:
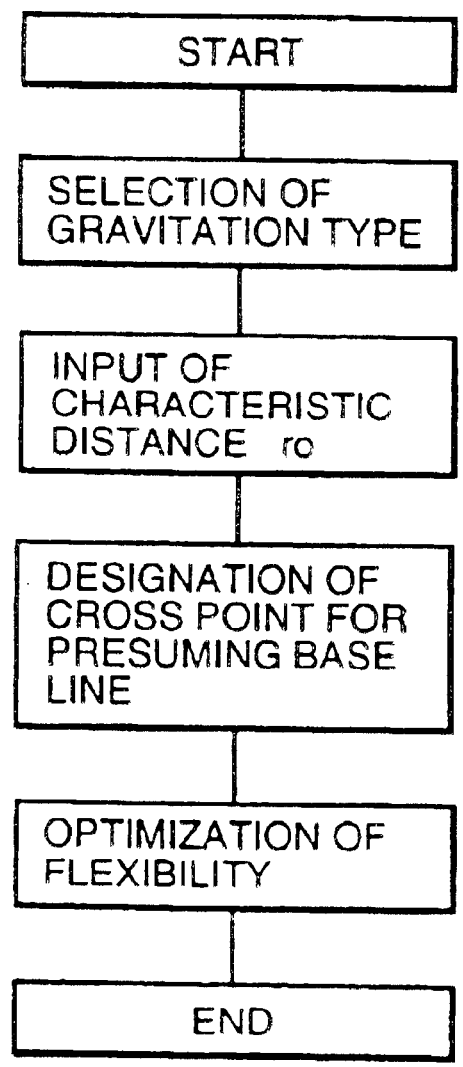
FIG. 28 is a flowchart 2 showing the manual pick up method.

An example such that three kinds of base lines when respective flexibility i's used are overlaid and displayed is shown in FIGS. 13 and 25 (FIGS. 23 and 24). According to the manual pick up method, the proper base line can be selected from the various base lines displayed on the CRT as shown in FIG. 13. Further, by preliminarily picking up a presumed cross point of the base line, the optimum flexibility can be calculated (FIG. 28).

When the base line is determined as mentioned above, a quantitative calculating process follows. A height or area is used as a peak size. When the calculation is executed on the basis of the peak height, a value obtained by subtracting a base line $Y_i$ from a signal value $Y_i$ at a point where the peak is largest is set to the peak height (FIG. 3).

When the calculation is executed on the basis of the peak area, an area calculation is performed according to the trapezoidal rule or Simpson's rule after obtaining $Y_i-y_i$ with respect to all of points in the peak area.

It is often necessary to confirm reliability of an obtained quantitative value. As shown in FIG. 14, coefficients of variation or a relative standard deviation of the quantitative value in each of the flexibilities are output in a format of a table, so that the reproducibility of the quantitative value can be recognized. It will be understood from the table that good reproducibility can be obtained when the medium flexibility is selected in the case.

In addition to the table in which the reproducibility is arranged for every flexibility, a table in which various quantitative methods are compared is also effective. For example, the quantitative method based on the peak area and that based on the peak height, or the conventional base line correcting method and the method according to the invention can be compared.

When the base line is formed or corrected, since the base line in which the two characteristics of the base line such that the base line is strongly attracted to the area having the small signal value expressed by the chromatogram and that adjacent points among continuous points which form the base line are loosely bound are considered can be formed, the base line which is more natural and is not influenced by noise and the like can easily be drawn by anyone and the base line that is always stable can easily be provided without a special operation by the operator.

By introducing the index of the flexibility that is one of the characteristics of the baseline, the base line which is not the conventional temporary base line like a graph of polygonal line but of a more natural and smooth curve can be obtained.

Although the base line has conventionally been corrected on the basis of differential characteristic points of a signal such as starting and ending points of a peak, trough between peaks, and the like, the base line which is not especially influenced by the fluctuation of such kinds of characteristic points can be obtained in the invention, so that the method is not much affected by local changes and noises.

Thus, the peak size can be accurately determined and the stable quantitative calculation can be always executed.

What is claimed is:

1. A chromatograph comprising:
   a detector for detecting a sample so as to output a measuring signal according to elapsed time,
   an input unit for inputting a strength parameter characterizing a form of base line by an operator,
   a data processor for processing said measuring signal based on said information signal so as to output a chromatogram formed with a plurality of chromatogram data points and a base line corresponding to said chromatogram, said data processor correcting a plurality of data points forming said base line based on said strength parameter, said strength parameter defining a difference in a direction of signal strength of said chromatogram between adjacent data points of said base line, and
   a display for displaying said chromatogram and said base line, said display having a strength parameter display area for displaying said difference in a direction of signal strength of said chromatogram between said adjacent data points of said base line.

2. A chromatograph comprising:
   a detector for detecting a sample so as to output a measuring signal according to elapsed time,
   an input unit for inputting a strength parameter characterizing a form of base line by an operator,
   a data processor for processing said measuring signal based on said information signal so as to output a chromatogram formed with a plurality of chromatogram data points and a base line corresponding to said chromatogram for correcting a plurality of data points forming said base line based on a first relation such that a difference between a signal data point of said chromatogram and a data point of said base line corresponding to said chromatogram and/or a second relation such that a difference in a direction of signal strength of said chromatogram between adjacent data points of said base line, for connecting between said corrected base lines by the spline interpolation method, and
   a display for displaying said chromatogram and said base line, said display having a flexibility display area for displaying said difference in direction of signal strength of said chromatogram between said adjacent data points of said base line.

* * * * *